US012773559B2

(12) United States Patent
Chalupper et al.

(10) Patent No.: US 12,773,559 B2
(45) Date of Patent: Oct. 27, 2026

(54) COCHLEAR IMPLANT SYSTEMS AND METHODS FOR ELECTRICAL COCHLEA STIMULATION

(71) Applicant: Advanced Bionics LLC, Valencia, CA (US)

(72) Inventors: Josef Chalupper, Paunzhausen (DE); Volkmar Hamacher, Hannover (DE)

(73) Assignee: Advanced Bionics LLC, Valencia, CA (US)

( * ) Notice: Subject to any disclaimer, the term of this patent is extended or adjusted under 35 U.S.C. 154(b) by 687 days.

(21) Appl. No.: 18/197,410

(22) Filed: May 15, 2023

(65) Prior Publication Data

US 2024/0382760 A1 Nov. 21, 2024

(51) Int. Cl.
*A61N 1/36* (2006.01)
*A61N 1/05* (2006.01)

(52) U.S. Cl.
CPC ....... *A61N 1/36178* (2013.01); *A61N 1/0541* (2013.01); *A61N 1/36192* (2013.01)

(58) Field of Classification Search
CPC .............. A61N 1/0541; A61N 1/36038; A61N 1/36178; A61N 1/36192
See application file for complete search history.

*Primary Examiner* — Amanda K Hulbert
(74) *Attorney, Agent, or Firm* — ALG Intellectual Property, LLC

(57) ABSTRACT

An exemplary cochlear implant system comprises an electrode array comprising a plurality of stimulation electrodes; a frequency filtering unit configured to divide an input audio signal into a plurality of input signal channels; and a stimulation control unit configured to generate from the plurality of input signal channels a dedicated stimulation signal for each of a plurality of stimulation channels, each stimulation channel being associated with one of the electrodes. The stimulation control unit is further configured to provide at least a subgroup of electrodes with stimulation signals, each of which is windowed in such a manner that at a time only to one of the electrodes of the subgroup, or only to non-adjacent electrodes of the subgroup, an active window is awarded during which the respective electrode is supplied with stimulation current. The stimulation signals of the electrode subgroup comprise (i) analog waveforms or wavelets which each correspond to a waveform of the input signal of a respective input signal channel associated with the respective stimulation channel, or (ii) pulse trains having an amplitude modulated by an amplitude of a waveform of the input signal of a respective input signal channel associated with the respective stimulation channel.

22 Claims, 5 Drawing Sheets

COCHLEAR IMPLANT SYSTEMS AND METHODS FOR ELECTRICAL COCHLEA STIMULATION

BACKGROUND INFORMATION

To enable good localization and speech understanding in noise, interaural time differences ("ITDs") and pitch are used in acoustic hearing. Current pulsatile stimulation strategies in cochlear implants, however, discard temporal fine structure and instantaneous frequency and therefore do not allow accurate perception of ITDs and pitch. Current analog stimulation strategies (which use stimulation waveforms corresponding to waveforms of the respective input signal) generate overlaps of electrical fields of electrodes which degrades or even eliminates the benefit of preserved temporal fine-structure and instantaneous frequency. In addition, the power consumption of analog stimulation strategies is significantly higher than in non-simultaneous coding strategies, since all available electrodes stimulate permanently. Since the power consumption of the implant is directly related to the size of the speech processor, the power efficiency of coding strategies is of high importance to offer small and cosmetically attractive speech processors.

Currently, both (simultaneous) analog and non-simultaneous pulsatile coding strategies are used in cochlear implants. Analog stimulation (e.g. SAS (simultaneous analog sampler)) has the advantage to preserve temporal fine structure and instantaneous frequency, but has the disadvantage of generating large overlaps between adjacent electrodes. With non-simultaneous coding (e.g. CIS (continuous interleaved sampling), a better electrode separation is achieved, but temporal fine structure and instantaneous frequency (i.e. frequency modulation within one analysis band) is not preserved as only the envelope is used to modulate pulsatile patterns. Depending on the coupling of the electrodes to the auditory nerve and number of spiral ganglion cells, patients may benefit more from non-simultaneous or simultaneous stimulation. Generally speaking, simultaneous stimulation may prohibit extraction of auditory cues due to overlapping electrical fields.

Interaural time differences (ITDs) play a crucial role to improve speech understanding in noise and localization in acoustic hearing (this applies both to normal hearing persons and hearing aid users). With bimodal stimulation, cochlear implant patients have access to temporal fine-structure (at least at low frequencies) in the non-implanted ear. However, to be able to use ITDs, the availability of temporal fine-structure is also required in the implanted ear.

U.S. Pat. No. 6,289,247 B2 relates to cochlear implant stimulation strategies including stimulation modes, like a hybrid analog pulsatile mode, which use simultaneous analog stimulation for the most apical electrodes and a CIS strategy for the other electrodes.

U.S. Pat. No. 10,707,836 B2 and the article "MED-EL Cochlear Implants: State of the Art and a Glimpse Into the Future", by I. Hochmair et al., in: Trends in Amplification, Volume 10, Number 4, December 2006 pp. 201-220 relate to a cochlear implant stimulation strategy for the most apical electrodes wherein at the zero crossings of the analog waveform of the input signal channel a Channel Specific Sampling Sequence (CSSS) formed by a short pulse train having an amplitude given by the envelope of the analog waveform and having a length given by the band pass frequency of the channel.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
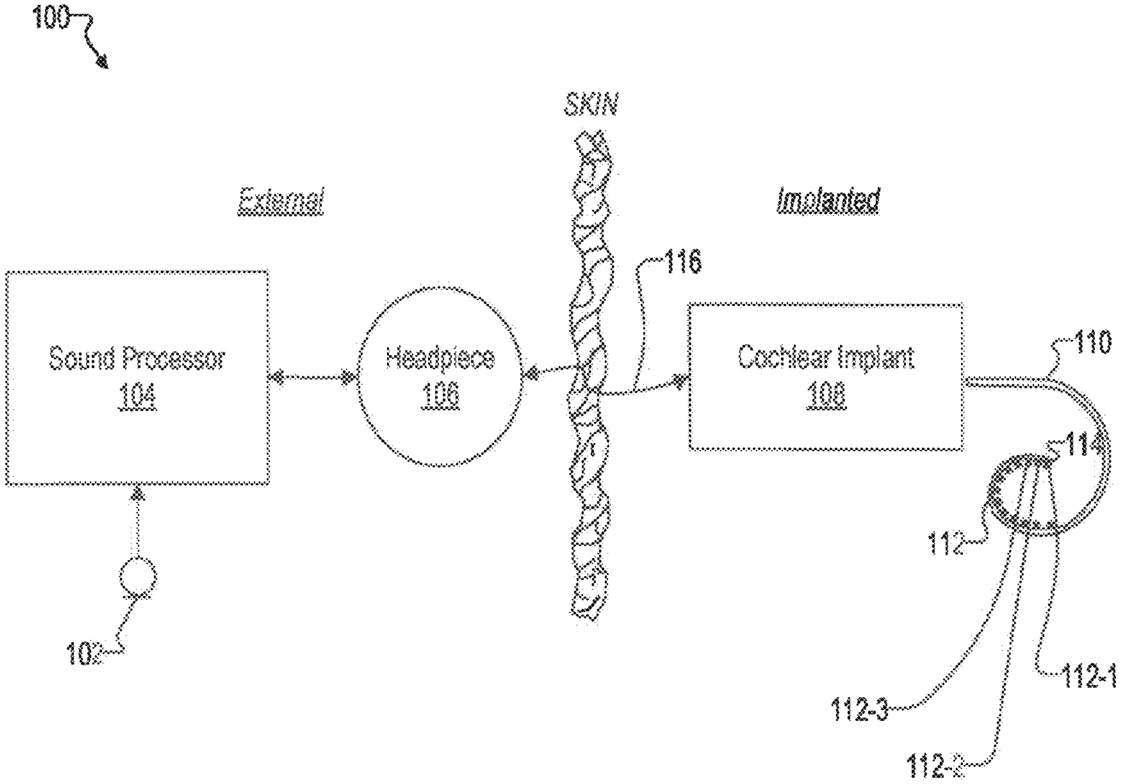
FIG. 1 illustrates an exemplary cochlear implant system according to principles described herein.

Cochlear implant systems and methods for electrical cochlea stimulation are described herein. For example, as described herein, a cochlear implant system may comprise an electrode array comprising a plurality of stimulation electrodes, a frequency filtering unit configured to divide an input audio signal into a plurality of input signal channels and a stimulation control unit configured to generate from the plurality of input signal channels a dedicated stimulation signal for each of a plurality of stimulation channels, each stimulation channel being associated with one of the electrodes. The stimulation control unit may be further configured to provide at least a subgroup of electrodes with stimulation signals, each of which is windowed in such a manner that at a time only to one of the electrodes of the subgroup, or only to non-adjacent electrodes of the subgroup, an active window is awarded during which the respective electrode is supplied with stimulation current. The stimulation signals of the electrode subgroup may comprise (i) analog waveforms or wavelets which each correspond to a waveform of the input signal of a respective input signal channel associated with the respective stimulation channel, or (ii) pulse trains having an amplitude modulated by an amplitude of a waveform of the input signal of a respective input signal channel associated with the respective stimulation channel.

A method of stimulating a patient's cochlea by an electrode array comprising a plurality of electrodes, may comprise dividing an input audio signal into a plurality of input signal channels and generating from the plurality of input signal channels a dedicated stimulation signal for each of a plurality of stimulation channels, each stimulation channel being associated with one of the electrodes. At least a subgroup of adjacent electrodes may be provided with stimulation signals, each of which is windowed in such a manner that at a time only to one of the electrodes of the subgroup, or only to non-adjacent electrodes of the subgroup, an active window is awarded during which the respective stimulation channel is supplied with stimulation current. The stimulation signals of the electrode subgroup may comprise (i) analog waveforms or wavelets which each correspond to a waveform of the input signal of a respective input signal channel associated with the respective stimulation channel, or (ii) pulse trains having an amplitude modulated by an amplitude of a waveform of the input signal of a respective input signal channel associated with the respective stimulation channel.

The systems and methods described herein may include a new stimulation strategy at least for a subgroup of the electrodes, for example formed by a number of the most apical electrodes, wherein a conventional simultaneous analog stimulation is replaced by a windowed stimulation wherein the electrodes of the subgroup are supplied sequentially with an analog stimulation waveform or wavelet or with a pulse train having an amplitude modulated by the amplitude-rather than by the envelope—of the analog waveform in such a manner that at a time only a single electrode—or at least only non-adjacent electrodes (which are sufficiently spaced apart from each other)—is or are active due to a dynamic across-electrode windowing mechanism.

In contrast to prior art, such windowed stimulation strategy allows to preserve temporal fine structure and instantaneous frequency and to avoid spectral overlap. As ITD cues are of particular importance at frequencies below 1.5 kHz, one may use the windowed stimulation at apical electrodes and pulsatile coding (e.g., CIS) at basal electrodes.

FIG. 1 illustrates an exemplary cochlear implant system 100. As shown, cochlear implant system 100 may include a microphone 102, a sound processor 104, a headpiece 106 having a coil disposed therein, a cochlear implant 108, and an electrode lead 110. Electrode lead 110 may include an array of electrodes 112 disposed on a distal portion of electrode lead 110 and that are configured to be inserted into a cochlea of a recipient to stimulate the cochlea when the distal portion of electrode lead 110 is inserted into the cochlea. One or more other electrodes (e.g., including a ground electrode, not explicitly shown) may also be disposed on other parts of electrode lead 110 (e.g., on a proximal portion of electrode lead 110) to, for example, provide a current return path for stimulation current generated by electrodes 112 and to remain external to the cochlea after electrode lead 110 is inserted into the cochlea. As described herein, electrode lead 110 may be naturally precurved or straight. Additional or alternative components may be included within cochlear implant system 100 as may serve a particular implementation.

As shown, cochlear implant system 100 may include various components configured to be located external to a recipient including, but not limited to, microphone 102, sound processor 104, and headpiece 106. Cochlear implant system 100 may further include various components configured to be implanted within the recipient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 may be housed within any suitable housing (e.g., a behind-the-ear ("BTE") unit, a body worn device, headpiece 106, and/or any other sound processing unit as may serve a particular implementation). Sound processor 104 may be configured to direct cochlear implant 108 to generate and apply electrical stimulation (e.g., a sequence of stimulation pulses) by way of one or more electrodes 112.

As shown, electrodes 112 may include a first electrode 112-1 that is most distally positioned on electrode lead 110 (i.e., closest to a distal end 114 of electrode lead 110), a second electrode 112-2 adjacent to electrode 110-1, a third electrode 112-3 adjacent to electrode 112-2, etc. Any number of electrodes 112 (e.g., sixteen) may be disposed on electrode lead 110 as may serve a particular implementation. While electrodes 112 are shown as linearly positioned along a side of electrode lead 110 that faces a modiolar wall of cochlea 200, other configurations for electrodes 112 may be implemented. For example, diametrically opposed electrodes 112 may be implemented (e.g., a first electrode and a second electrode may be positioned diametrically to one another, while a third and fourth electrode may be positioned diametrically to one another and linearly following first and second electrodes). As another example, the distal-most electrode may be a tip electrode (i.e., located a distal end 114 of electrode 110).

In some examples, sound processor 104 may direct cochlear implant 108 to apply electrical stimulation representative of an audio signal presented to the recipient. The audio signal may be detected by microphone 102, input by way of an auxiliary audio input port, input by way of a clinician's programming interface (CPI) device, and/or otherwise provided to sound processor 104. Sound processor 104 may process the audio signal in accordance with a selected sound processing strategy or program to generate appropriate stimulation parameters for controlling cochlear implant 108.

Additionally or alternatively, sound processor 104 (and/or any other suitable computing device) may direct cochlear implant 108 to generate and apply electrical stimulation that is not representative of audio signals to the patient. For example, as described herein, sound processor 104 and/or any other suitable computing device may direct cochlear implant 108 to apply a sequence of stimulation pulses by way of one or more electrodes 112 during a lead insertion procedure.

In some examples, sound processor 104 may wirelessly transmit stimulation parameters (e.g., in the form of data words included in a forward telemetry sequence) and/or power signals to cochlear implant 108 by way of a wireless communication link 116 between headpiece 106 and cochlear implant 108 (e.g., a wireless link between a coil disposed within headpiece 106 and a coil physically coupled to cochlear implant 108). It will be understood that communication link 116 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the recipient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via communication link 116.

Cochlear implant 108 may include any suitable type of implantable stimulator. For example, cochlear implant 108 may be implemented by an implantable cochlear stimulator. Additionally or alternatively, cochlear implant 108 may include a brainstem implant and/or any other type of cochlear implant that may be implanted within a recipient and configured to apply stimulation to one or more stimulation sites located along an auditory pathway of a recipient.

In some examples, cochlear implant 108 may be configured to generate electrical stimulation in accordance with one or more stimulation parameters transmitted thereto by sound processor 104. Cochlear implant 108 may be further configured to apply the electrical stimulation to one or more electrodes 112 disposed along electrode lead 110. Such stimulation may be configured as monopolar stimulation (e.g., stimulation applied by way of a single electrode 112 with a remote electrode on a case of cochlear implant 108 or on a proximal portion of electrode lead 108 being used as a return electrode) or as multipolar stimulation (e.g., bipolar stimulation applied via by way of two electrodes 112). In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
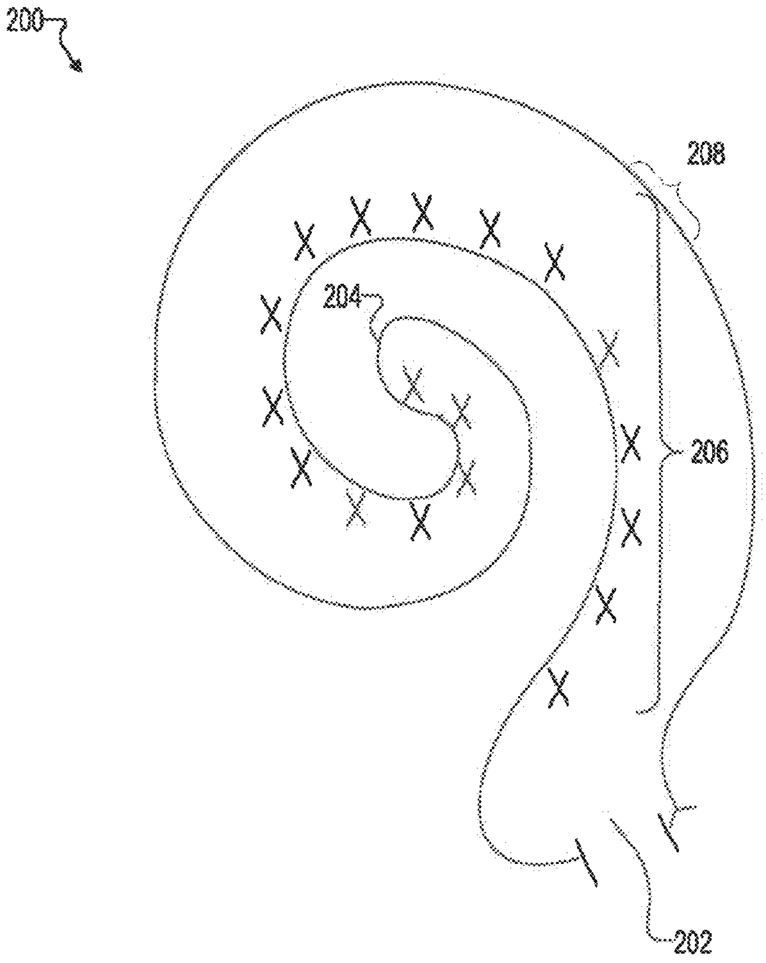
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue, which is denoted by Xs in FIG. 2. The auditory nerve tissue is organized within the cochlea 200 in a tonotopic manner. Relatively low frequencies are encoded at or near the apex 204 of the cochlea 200 referred to as an "apical region" while relatively high frequencies are encoded at or near the base 202 in a basal region 206 of the cochlea 200.

FIG. 2 illustrates a region of cochlea 200 referred to as a basal turn 208. As shown, basal turn 208 is located at an end of basal region 206. As described herein, the systems and methods are configured to determine, in real-time during a lead insertion procedure, when distal end 114 of electrode lead 110 is within a threshold distance of basal turn 208 (e.g., when distal end 114 of electrode lead 110 is approaching but not yet at basal turn 208, at basal turn 208, or slightly past basal turn 208). In so doing, it may be possible for an operator to begin removal of a stylet holding electrode lead 110 in a straightened configuration, as well as to avoid damage (e.g., scraping or puncture) of cochlea 200 by electrode lead 110 and/or the stylet.

Figure 3:
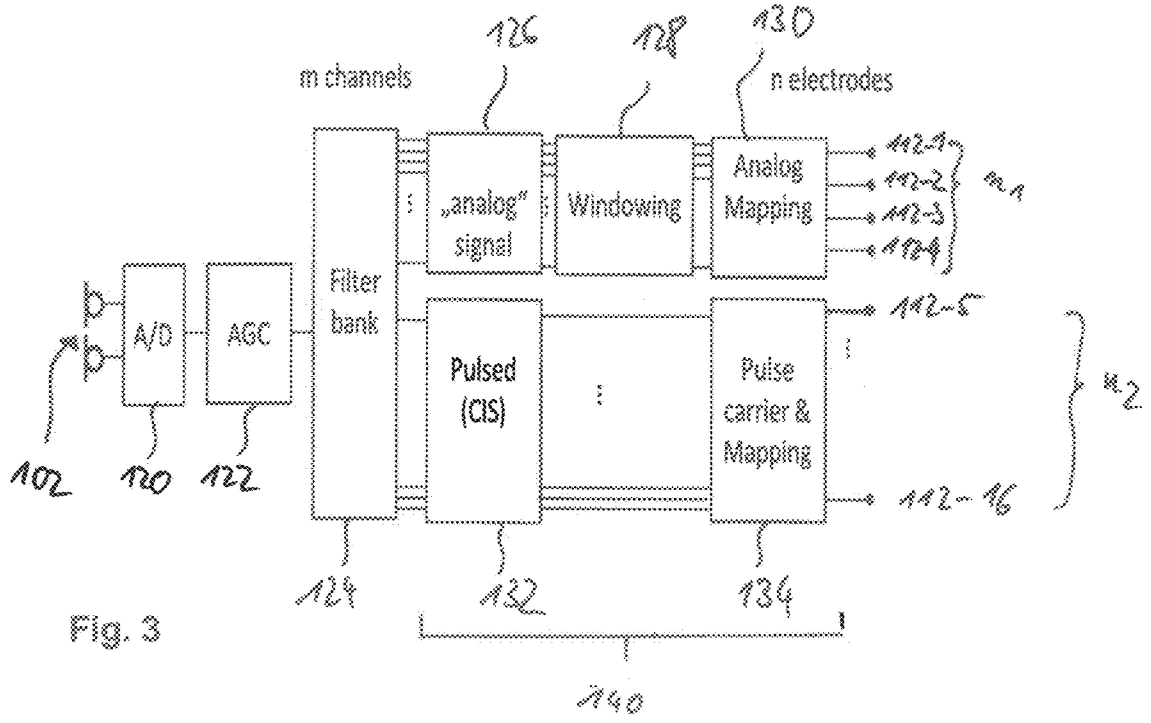
FIG. 3 illustrates an exemplary signal processing schema of a cochlear implant system according to principles described herein.

FIG. 3 illustrates an exemplary signal processing schema for a cochlear implant system, such as the cochlear implant system 100 of FIG. 1, wherein the input audio signal captured by the microphone 102 undergoes analog-to-digital conversion in an A/D-converter 120, and thereafter a gain model is applied in an automatic gain control (AGC) unit 122. The input audio signal then is supplied to a frequency filtering unit, such as a filterbank 124, which divides the input audio signal into a plurality of m input signal channels. For example, the frequency filtering unit may comprise a plurality of bandpass filters, wherein each of the bandpass filters may define one of the m input signal channels. Alternatively, the frequency filtering unit may comprise a plurality of Fast Fourier Transform (FFT) filters for defining the m input signal channels.

Figure 5:
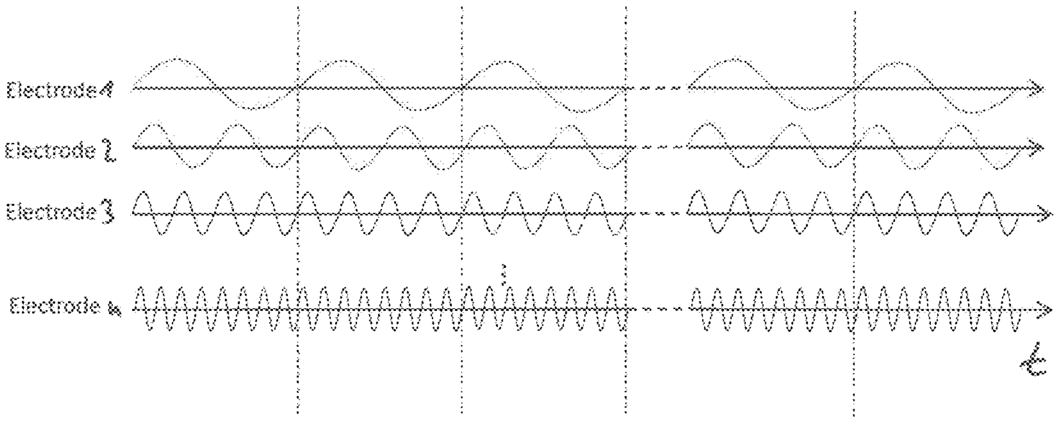
FIG. 5 illustrates exemplary analog electrode stimulation signals of a cochlear implant system of the prior art.
Figure 6:
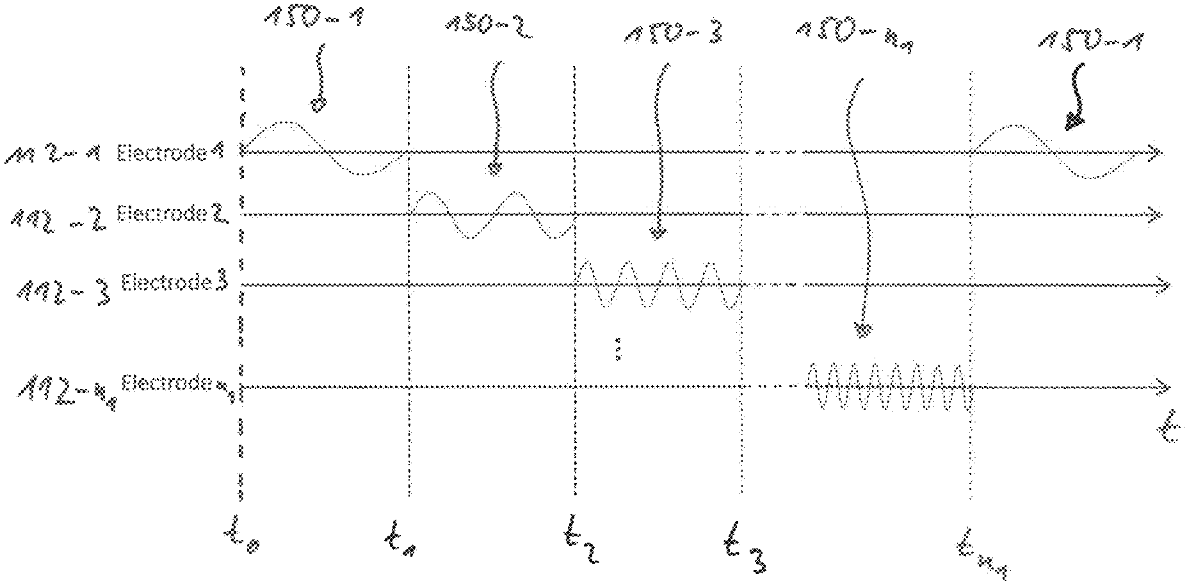
FIG. 6 illustrates exemplary windowed analog electrode stimulation signals of a cochlear implant system according to principles described herein.
Figure 7:
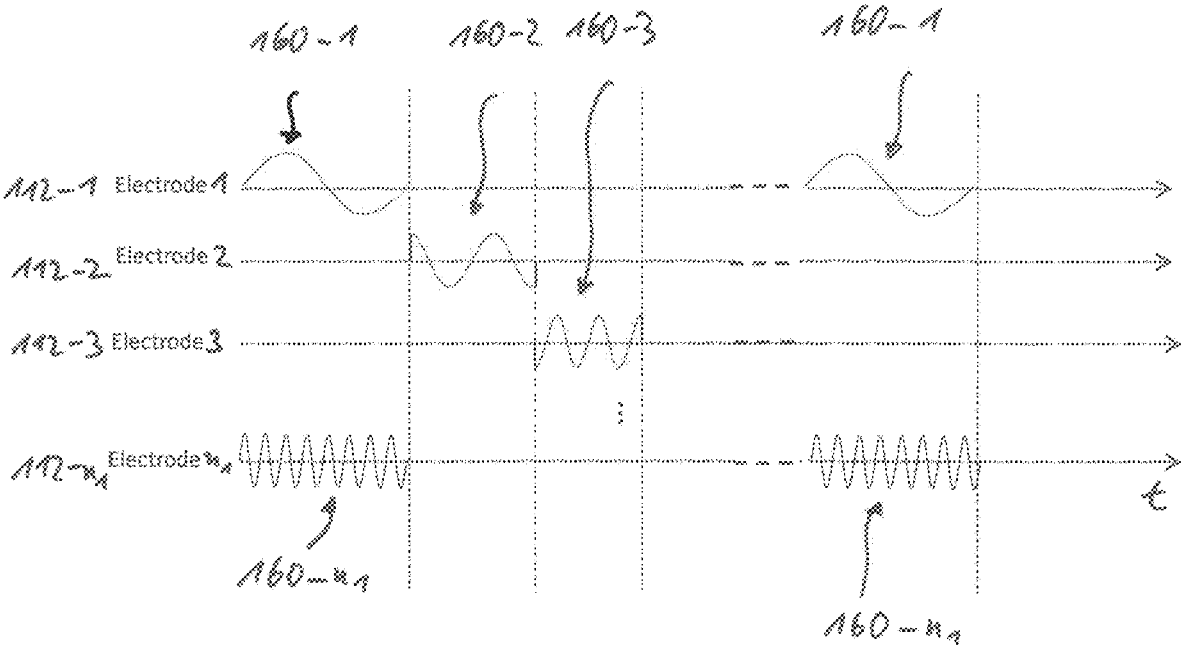
FIG. 7 illustrates another example of windowed analog electrode stimulation signals of a cochlear implant system according to principles described herein.

A first portion $m_1$ of the m input signals may be supplied to a first signal processing unit 126 which generates an "analog" signal for each of the $m_1$ input signals, e.g., from the output signal of the respective bandpass filter or from the real part of the FFT signal in the respective input signal channel. The term "analog" is used here to indicate that the—actually digital—signal is determined by the amplitude of the signal of the respective input signal channel but not by the envelope of the signal of the respective input signal channel). For example, the analog signal may comprise analog waveforms or wavelets which each correspond to a waveform of the signal of the respective input signal channel, or it may comprise pulse trains having an amplitude modulated by the amplitude of a waveform of the input of the respective input signal channel. The "analog" signals are supplied to a windowing unit 128 which applies active windows to the analog signals in such a manner that ensures that there is no simultaneous stimulation by adjacent electrodes 112 (the windowing procedure is illustrated in FIGS. 5 to 7 discussed below). The windowed "analog" signals are supplied to an "analog" or first mapping unit 130 which maps the $m_1$ input signals/channels to a subgroup of $n_1$ electrodes of the n electrodes (each of the electrodes 112 corresponds to a stimulation channel). In the example of the FIG. 3, the subgroup of electrodes is formed by the four most apical electrodes 112-1, 112-2, 112-3 and 112-4, i.e., $n_1=4$.

A second portion $m_2$ of the m input signals may be supplied to a second signal processing unit 132 which generates non-simultaneous pulsed stimulation signals, e.g., formed by continuous interleaved sampling (CIS), which are supplied to a second mapping unit 134 which provides a pulse carried for the CIS signals and which maps the CIS signals to the remaining $n_2$ electrodes 112-5 to 112-16 which do not form part of the subgroup of $n_1$ electrodes.

The units 126, 128, 130, 132 and 134 may be considered to act together as a stimulation control unit 140.

Figure 4:
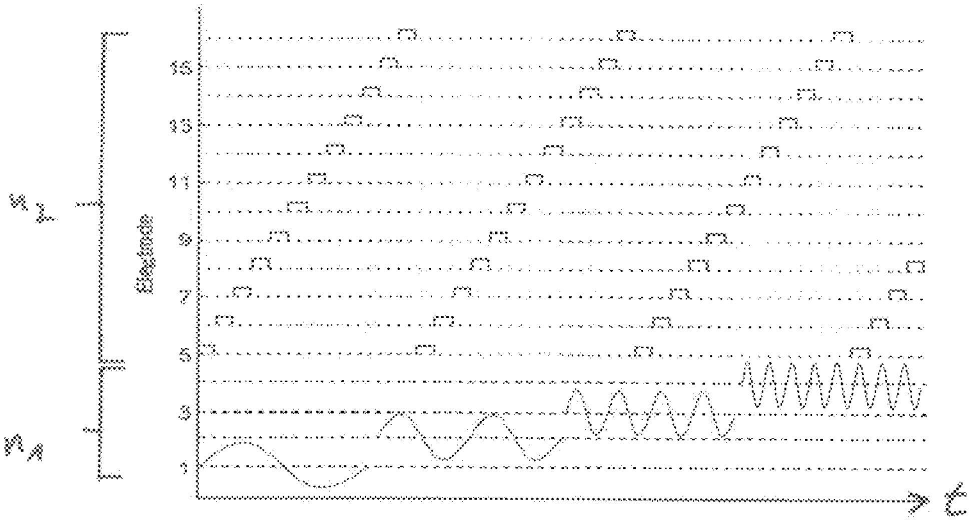
FIG. 4 illustrates an exemplary implementation of electrode stimulation signals of the cochlear implant system of FIG. 3 according to principles described herein.

The resulting stimulation signals of the electrodes 112-1 to 112-16 are schematically illustrated in FIG. 4 (signal amplitude as a function of time).

FIG. 5 illustrates exemplary analog stimulation signals of the prior art, wherein the stimulation current amplitude is shown as a function of time for each electrode. In the example of FIG. 5 each electrode is supplied simultaneously and continuously with a stimulation signal corresponding to an "analog" waveform, such as a SAS signal, as obtained from bandpass filtering or FFT-bins of the input audio signal. As already mentioned above, such analog simultaneous stimulation, compared to non-simultaneous pulsed stimulation, has the advantage to preserve temporal fine structure and instantaneous frequency but has the disadvantage of generating large overlaps between adjacent electrodes.

FIG. 6 illustrates exemplary windowed analog stimulation signals which prevent overlaps between adjacent electrodes while preserving temporal fine structure and instantaneous frequency. This is achieved by sequentially awarding an active window to the electrodes/stimulation channels, with each electrode being supplied with stimulation current only during the duration of the active window. The active window sequentially passes across the stimulation channels in a manner so as to implement a dynamic across-electrode windowing, with the electrodes being supplied sequentially with a stimulation signal only for the duration of the active window. It is to be understood that the window in principle may have any appropriate shape; for example, it may have a rectangular shape or it may be of a "fade-in/fade-out" type, such as a Hanning window.

In the example illustrated in FIG. 6 the windowed analog stimulation is applied to $n_1$ electrodes, wherein the active window is applied or awarded at time $t_0$ to the first electrode 112-1 (which may the most apical electrode) and lasts until time $t_1$, so that first electrode 112-1 is provided with an analog continuous stimulation signal 150-1 during that time period, with the analog continuous signal 150-1 being switched off at time $t_1$. Then the active window moves to the second electrode 112-2 which is supplied with an analog continuous stimulation signal 150-2 from time $t_1$ to time $t_2$, with the stimulation current of the second electrode starting at time $t_1$, and then to the third electrode 112-3, etc., Once the active window for the last electrode 112-$n_1$ of the group of $n_1$ electrodes has terminated at time $t_{n1}$, the sequence starts again with the first electrode 112-1.

Thus, in contrast to the conventional stimulation (SAS) illustrated in FIG. 5, with the non-simultaneous stimulation approach illustrated in FIG. 6 only one electrode is stimulated at a time, while the waveform may be exactly the same as in conventional SAS. Such can be regarded as a dynamic across-electrode gating (or windowing) mechanism which makes sure that not all electrodes open their gate to transmit (i.e., let pass) their bandpass signal simultaneously.

In cochlear electrode stimulation charge balancing of the stimulation current has to be ensured for each electrode and each stimulation window to avoid harm of tissue and neural structures caused by direct-current.

In some implementations, charge balancing may be achieved by adjusting the active window length accordingly. According to one example, as illustrated in FIG. 6, the length of the active window may be adjusted by monitoring zero crossings of the stimulation signal of the respective stimulation channel. For example, the active window may start with a zero crossing of the stimulation signal of the respective stimulation channel (e.g., stimulation signal 150-1 the first electrode 112-1 has a zero crossing at time $t_0$) and may terminate an even number of subsequent zero-crossings of the stimulation signal of the respective stimulation channel later (e.g. at time $t_1$ for the first electrode 112-1 after two more zero crossing). In the example of FIG. 6, the active window lasts for all channels two more zero-crossings after the initial zero-crossing, so that the active window lasts for one full period (360 degrees)/wavelength of the stimulation waveform. Such adjustment of the active window has to be implemented for each electrode/stimulation channel, which means that the window length depends on the (main) frequency of the respective channel and hence usually will be different for each channel.

When zero crossings are used for charge balancing, as in FIG. 6, the wavelets may have different durations or comprise a different number of periods, as period durations/wavelengths are decreasing with increasing frequencies. The result will be signal-adaptive gate lengths (active window lengths) and electrode specific stimulation rates.

Another example of windowed analog stimulation is illustrated in FIG. 7, wherein the use of a charge integration unit allows to increase stimulation rate, e.g., to account for patient or situation-specific needs. In this example, at any time a gate can be opened but it will not be closed until the integrated charge as determined by the integration unit amounts to zero, allowing for an adjustable electrode-specific stimulation rate. In other words, the length of the active window may be adjusted by integrating the charge delivered by the stimulation signal in the respective stimulation channel since the start of the active window, with the active window being terminated once the integrated charge is found to be balanced.

In the example of FIG. 7 electrode-specific wavelets 160-1, 160-2, 160-3, . . . 160-$n_1$ are illustrated, wherein the first electrode 112-1 and the last electrode 112-$n_1$ stimulate for one full period, as in FIG. 6, the second and third electrodes 112-2, 112-3 stimulate only for a half-period (i.e., the active window includes only a single zero crossing of the stimulation signal), starting with the maximal current in the "plus direction" (electrode 112-2) or the "minus direction" (electrode 112-3).

It is to be noted that in the example of FIG. 7—in contrast to the example of FIG. 6—the first electrode 112-1 and the last electrode 112-$n_1$ are stimulated simultaneously, i.e., an active window is awarded to both electrodes simultaneously. However, since these electrodes are spaced apart by a relatively large distance, no detrimental stimulation overlap will result from such simultaneous stimulation.

In some implementations, charge balancing may be achieved by determining a suitable fixed length of the active window for each stimulation channel upon fitting of the system based on the cross-over frequencies of the stimulation channels. For example, when in the example of FIG. 6 the (main) frequency of each stimulation channel is known and constant, the duration of the active window required for each electrode for charge balancing can be calculated based on the channel frequency, so that it is not necessary to monitor zero crossings.

In some implementations, charge balancing may be achieved by adding non-perceivable subthreshold pulses during the active window in an amount necessary for charge balancing.

It is to be noted that stimulation by the analog waveforms or wavelets during the active window may occur as monopolar stimulation or as multipolar stimulation. During monopolar stimulation the electrodes adjacent to the electrode to which the active window is presently awarded do not carry return current from the active electrode, while an extra-cochlear electrode acts as a return electrode. During multipolar stimulation at least one of the electrodes adjacent to the presently active electrode is supplied with an inverted copy of the stimulation signal applied by the presently active electrode so as to act as a return electrode. Bipolar stimulation means that only one of the two electrodes adjacent to the presently active electrode acts as return electrode (wherein the inverted copy of the stimulation signal has the same amplitude as the stimulation signal). Tripolar stimulation means that both electrodes adjacent to the presently active electrode acts as return electrode (wherein the inverted copy of the stimulation signal for each of the adjacent electrodes has the half the amplitude of the stimulation signal).

Figure 9:
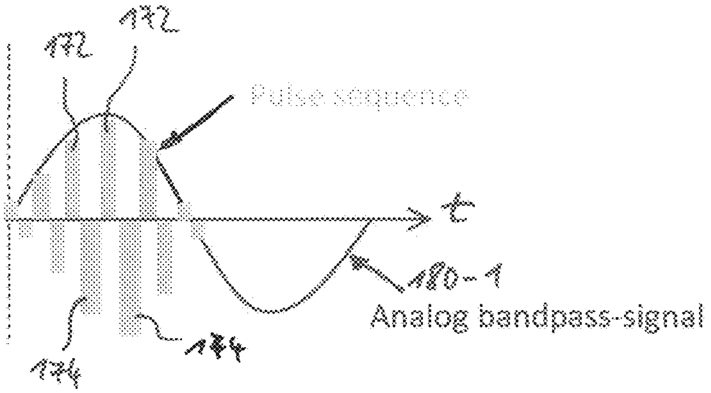
FIG. 9 illustrates exemplary windowed pulse train electrode stimulation signals of a cochlear implant system according to principles described herein.

In some implementations, the stimulation signals may be formed by pulse trains having an amplitude modulated by the amplitude of a waveform of the input signal of a respective input signal channel associated with the respective stimulation channel. An example of such pulse train signal is illustrated in FIG. 9, wherein a pulse train 170-1 is formed by a sequence of alternating positive and negative pulses 172, 174 has an amplitude modulated by the amplitude of an analog continuous waveform 180-1 (which in the example of FIG. 9 has a length of one period/wavelength).

It is to be understood that such pulse train signals may replace the windowed analog continuous waveforms/wavelets of the examples of FIGS. 6 and 7 (e.g., the pulse train 170-1 may replace the waveform 150-1 of FIG. 6 or the waveform 160-1 of FIG. 7). In other words, the pulse trains signals may be windowed in the same way as the analog continuous waveforms, so as to prevent simultaneous stimulation of adjacent electrodes.

One benefit of the pulse train signals is that they allow for a higher pulse rate/stimulation rate compared to the analog continuous waveforms. For example, the pulse rate of the pulse trains may be at least 5 times the instantaneous frequency of the input signal in the associated input signal channel.

In some implementations, the pulse rate of the pulse trains of the stimulation signal of a respective stimulation channel may be modulated by the instantaneous frequency of the input signal in the associated input signal channel.

Figure 8:
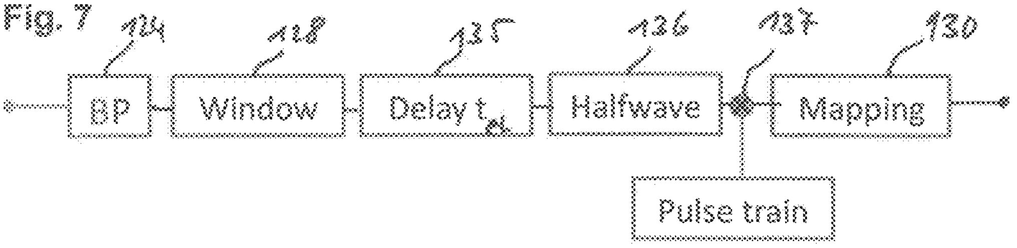
FIG. 8 illustrates an exemplary signal processing schema for generating windowed pulse train electrode stimulation signals of a cochlear implant system according to principles described herein.

FIG. 8 illustrates an exemplary signal processing schema for generating windowed pulse train electrode stimulation signals. As in FIG. 3, the input signal captured by a microphone 102, after having been converted in an A/D converter 120 and after having been treated in an AGC unit 122, is divided into a plurality of input signal channels, each providing a continuous "analog" waveform, by a frequency filtering unit 124. The continuous "analog" waveform is windowed, as in the examples of FIGS. 6 and 7, in a windowing unit 128. A delay ter is applied to the windowed signal in a delay unit 135 (the delay shall mimic the delay due the travelling wave on basilar membrane of a healthy cochlea; this is important in particular for bimodal CI recipients), and then the signal is supplied to a halfwave rectification unit 136 (halfwave rectification mimics the behavior of inner hair cells of a healthy cochlea). The output signal of the halfwave rectification unit 136 is used for being multiplied in a multiplier unit 137 with a pulse train generated in a pulse train unit 138, so as provide a windowed pulse train electrode stimulation signal, wherein the amplitude of the pulses is modulated by the amplitude of the respective continuous "analog" waveform provided by the frequency filtering unit 124. The resulting windowed pulse train stimulation signal is then supplied to a mapping unit 130 for mapping it with the respective stimulation channel/electrode.

As already mentioned above, interaural time differences (ITDs) play a crucial role to improve speech understanding in noise and localization in acoustic hearing, both for normal hearing persons and hearing aid users. With bimodal stimulation, cochlear implant patients have access to temporal fine-structure (at least at low frequencies) in the non-implanted ear. However, to be able use ITDs, the availability of temporal fine-structure is also required in the implanted ear. Therefore, windowed stimulation as described above will be beneficial, by providing for improved speech understanding in noise and localization, in particular for bimodal fittings (hearing aid at one ear and cochlear implant at the other ear) and bilateral fittings (cochlear implants at both ears).

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

The following aspects may be considered as one or more combinations of features contemplated herein. However, the following aspects are not to be considered limiting, and more or fewer features of each combination have also been contemplated.

Aspect 1. A system comprising:

an electrode array comprising a plurality of stimulation electrodes;

a frequency filtering unit configured to divide an input audio signal into a plurality of input signal channels; and a stimulation control unit configured to generate from the plurality of input signal channels a dedicated stimulation signal for each of a plurality of stimulation channels, each stimulation channel being associated with one of the electrodes;

wherein the stimulation control unit is further configured to provide at least a subgroup of electrodes with stimulation signals, each of which is windowed in such a manner that at a time only to one of the electrodes of the subgroup, or only to non-adjacent electrodes of the subgroup, an active window is awarded during which the respective electrode is supplied with stimulation current, and wherein the stimulation signals of the electrode subgroup comprise (i) analog waveforms or wavelets which each correspond to a waveform of the input signal of a respective input signal channel associated with the respective stimulation channel, or (ii) pulse trains having an amplitude modulated by an amplitude of a waveform of the input signal of a respective input signal channel associated with the respective stimulation channel.

Aspect 2. The system of aspect 1, wherein the active window passes sequentially across the stimulation channels of the subgroup of electrodes, thereby implementing a dynamic across-electrode windowing so that the electrodes of the subgroup are supplied sequentially with a stimulation signal for the duration of the window.

Aspect 3. The system of aspect 1, wherein the subgroup of electrodes comprises at least the two most apical electrodes.

Aspect 4. The system of aspect 3, wherein the subgroup of electrodes comprises not more than the eight most apical electrodes.

Aspect 5. The system of aspect 1, wherein the stimulation control unit is configured to provide at least some of the electrodes not forming part of the subgroup with non-simultaneous pulsed stimulation signals.

Aspect 6 The system of aspect 5, wherein said non-simultaneous pulsed stimulation signals are formed by continuous interleaved sampling (CIS).

Aspect 7. The system of aspect 1, wherein the stimulation signals of the subgroup of electrodes are analog waveforms or wavelets which are charge balanced by adjusting the length of the active window.

Aspect 8. The system of aspect 7, wherein the length of the active window is adjusted by monitoring zero crossings of the stimulation signal of the respective stimulation channel.

Aspect 9. The system of aspect 8, wherein the active window starts with a zero crossing of the stimulation signal of the respective stimulation channel and terminates an even number of subsequent zero-crossings of the stimulation signal of the respective stimulation channel.

Aspect 10. The system of aspect 7, wherein the length of the active window is adjusted by integrating the charge delivered by the stimulation signal in the respective stimulation channel since the start of the active window, and wherein the active window is terminated once the integrated charge is found to be balanced.

Aspect 11. The system of aspect 10, wherein the active window includes only a single zero crossing of the stimulation signal.

Aspect 12. The system of aspect 1, wherein the stimulation signals of the subgroup of electrodes are analog waveforms or wavelets and wherein the stimulation signals of the subgroup of electrodes are charge balanced by determining a suitable fixed length of the active window for each stimulation channel upon fitting of the system based on the cross-over frequencies of the stimulation channels.

Aspect 13. The system of aspect 1, wherein the stimulation signals of the subgroup of electrodes are analog waveforms or wavelets to which non-perceivable subthreshold pulses are added for achieving charge balancing during the active window when necessary.

Aspect 14. The system of aspect 1, wherein the pulse rate of the pulse trains of the stimulation signal of a respective stimulation channel of the subgroup of electrodes is at least 2 times the instantaneous frequency of the input signal in the associated input signal channel.

Aspect 15. The system of aspect 1, wherein the pulse rate of the pulse trains of the stimulation signal of a respective stimulation channel of the subgroup of electrodes is modulated by the instantaneous frequency of the input signal in the associated input signal channel.

Aspect 16. The system of aspect 1, wherein the frequency filtering unit comprises a plurality of bandpass filters.

Aspect 17. The system of aspect 16, wherein each of the band pass filters is provided for defining one of the input signal channels, and wherein the analog waveform is given by the output signal of the respective bandpass filter.

Aspect 18. The system of aspect 1, wherein the frequency filtering unit comprises FFT filters.

Aspect 19. The system of aspect 18, wherein the analog waveform is given by the real part of the FFT signal in the respective input signal channel.

Aspect 20. The system of aspect 1, wherein the active window is a rectangular window or a hanning window.

Aspect 21. The system of aspect 1, wherein stimulation by the analog waveforms or wavelets during the active window includes multipolar stimulation, wherein an inverted copy of the stimulation signal applied by the electrode to which the active window is presently awarded is applied by at least one adjacent electrode acting as a return electrode.

Aspect 22. A method of stimulating a patient's cochlea by an electrode array comprising a plurality of electrodes, the method comprising:

dividing an input audio signal into a plurality of input signal channels; and generating from the plurality of input signal channels a dedicated stimulation signal for each of a plurality of stimulation channels, each stimulation channel being associated with one of the electrodes;

providing at least a subgroup of adjacent electrodes with stimulation signals, each of which is windowed in such a manner that at a time only to one of the electrodes of the subgroup, or only to non-adjacent electrodes of the subgroup, an active window is awarded during which the respective stimulation channel is supplied with stimulation current, wherein the stimulation signals of the electrode subgroup comprise (i) analog waveforms or wavelets which each correspond to a waveform of the input signal of a respective input signal channel associated with the respective stimulation channel, or (ii) pulse trains having an amplitude modulated by an amplitude of a waveform of the input signal of a respective input signal channel associated with the respective stimulation channel.

What is claimed is:

1. A cochlear implant system, comprising an electrode array comprising a plurality of stimulation electrodes;

a frequency filtering unit configured to divide an input audio signal into a plurality of input signal channels; and a stimulation control unit configured to generate from the plurality of input signal channels a dedicated stimulation signal for each of a plurality of stimulation channels, each stimulation channel being associated with one of the electrodes;

wherein the stimulation control unit is further configured to provide at least a subgroup of electrodes with stimulation signals, each of which is windowed in such a manner that at a time only to one of the electrodes of the subgroup, or only to non-adjacent electrodes of the subgroup, an active window is awarded during which the respective electrode is supplied with stimulation current, and wherein the stimulation signals of the electrode subgroup comprise (i) analog waveforms or wavelets which each correspond to a waveform of the input signal of a respective input signal channel associated with the respective stimulation channel, or (ii) pulse trains having an amplitude modulated by an amplitude of a waveform of the input signal of a respective input signal channel associated with the respective stimulation channel.

2. The system of claim 1, wherein the active window passes sequentially across the stimulation channels of the subgroup of electrodes, thereby implementing a dynamic across-electrode windowing so that the electrodes of the subgroup are supplied sequentially with a stimulation signal for a duration of the window.

3. The system of claim 1, wherein the subgroup of electrodes comprises at least the two most apical electrodes.

4. The system of claim 3, wherein the subgroup of electrodes comprises not more than the eight most apical electrodes.

5. The system of claim 1, wherein the stimulation control unit is configured to provide at least some of the electrodes not forming part of the subgroup with non-simultaneous pulsed stimulation signals.

6. The system of claim 5, wherein said non-simultaneous pulsed stimulation signals are formed by continuous interleaved sampling (CIS).

7. The system of claim 1, wherein the stimulation signals of the subgroup of electrodes are analog waveforms or wavelets which are charge balanced by adjusting a length of the active window.

8. The system of claim 7, wherein the length of the active window is adjusted by monitoring zero crossings of the stimulation signal of the respective stimulation channel.

9. The system of claim 8, wherein the active window starts with a zero crossing of the stimulation signal of the respective stimulation channel and terminates an even number of subsequent zero-crossings of the stimulation signal of the respective stimulation channel.

10. The system of claim 7, wherein the length of the active window is adjusted by integrating the charge delivered by the stimulation signal in the respective stimulation channel since a start of the active window, and wherein the active window is terminated once the integrated charge is found to be balanced.

11. The system of claim 10, wherein the active window includes only a single zero crossing of the stimulation signal.

12. The system of claim 1, wherein the stimulation signals of the subgroup of electrodes are analog waveforms or wavelets and wherein the stimulation signals of the subgroup of electrodes are charge balanced by determining a suitable fixed length of the active window for each stimulation channel upon fitting of the system based on the cross-over frequencies of the stimulation channels.

13. The system of claim 1, wherein the stimulation signals of the subgroup of electrodes are analog waveforms or wavelets to which non-perceivable subthreshold pulses are added for achieving charge balancing during the active window when necessary.

14. The system of claim 1, wherein a pulse rate of the pulse trains of the stimulation signal of a respective stimulation channel of the subgroup of electrodes is at least two times an instantaneous frequency of the input signal in the associated input signal channel.

15. The system of claim 1, wherein a pulse rate of the pulse trains of the stimulation signal of a respective stimulation channel of the subgroup of electrodes is modulated by the instantaneous frequency of the input signal in the associated input signal channel.

16. The system of claim 1, wherein the frequency filtering unit comprises a plurality of bandpass filters.

17. The system of claim 16, wherein each of the bandpass filters is provided for defining one of the input signal channels, and wherein the analog waveform is given by the output signal of the respective bandpass filter.

18. The system of claim 1, wherein the frequency filtering unit comprises FFT filters.

19. The system of claim 18, wherein the analog waveform is given by a real part of an FFT signal in the respective input signal channel.

20. The system of claim 1, wherein the active window is a rectangular window or a hanning window.

21. The system of claim 1, wherein stimulation by the analog waveforms or wavelets during the active window includes multipolar stimulation, wherein an inverted copy of the stimulation signal applied by the electrode to which the active window is presently awarded is applied by at least one adjacent electrode acting as a return electrode.

22. A method of stimulating a patient's cochlea by an electrode array comprising a plurality of electrodes, the method comprising:

dividing an input audio signal into a plurality of input signal channels; and generating from the plurality of input signal channels a dedicated stimulation signal for each of a plurality of stimulation channels, each stimulation channel being associated with one of the electrodes;

providing at least a subgroup of adjacent electrodes with stimulation signals, each of which is windowed in such a manner that at a time only to one of the electrodes of the subgroup, or only to non-adjacent electrodes of the subgroup, an active window is awarded during which the respective stimulation channel is supplied with stimulation current, wherein the stimulation signals of the electrode subgroup comprise (i) analog waveforms or wavelets which each correspond to a waveform of the input signal of a respective input signal channel associated with the respective stimulation channel, or (ii) pulse trains having an amplitude modulated by an amplitude of a waveform of the input signal of a respective input signal channel associated with the respective stimulation channel.

* * * * *